(12) United States Patent
Barak et al.

(10) Patent No.: US 9,849,114 B2
(45) Date of Patent: Dec. 26, 2017

(54) OXYMETAZOLINE FOR THE TREATMENT OF ANO-RECTAL DISORDERS

(71) Applicant: RDD Pharma Ltd., Tel Aviv (IL)

(72) Inventors: Nir Barak, Tel Aviv (IL); Howard Lawrence Rice, Tel Aviv (IL)

(73) Assignee: RDD Pharma Ltd., Tel Aviv (IL)

( * ) Notice: Subject to any disclaimer, the term of this patent is extended or adjusted under 35 U.S.C. 154(b) by 0 days.

(21) Appl. No.: 15/168,432

(22) Filed: May 31, 2016

(65) Prior Publication Data

US 2016/0271110 A1 Sep. 22, 2016

Related U.S. Application Data

(60) Division of application No. 14/063,759, filed on Oct. 25, 2013, now abandoned, which is a continuation of application No. PCT/IL2012/050148, filed on Apr. 24, 2012.

(60) Provisional application No. 61/478,949, filed on Apr. 26, 2011.

(51) Int. Cl.
  *A61K 31/4174* (2006.01)
  *A61K 31/4164* (2006.01)
  *A61K 45/06* (2006.01)
  *A61K 9/00* (2006.01)

(52) U.S. Cl.
  CPC ........ *A61K 31/4174* (2013.01); *A61K 9/0031* (2013.01); *A61K 31/4164* (2013.01); *A61K 45/06* (2013.01)

(58) Field of Classification Search
  CPC .. A61K 31/4164; A61K 45/06; A61K 9/0031; A61K 31/4174
  See application file for complete search history.

(56) References Cited

U.S. PATENT DOCUMENTS 6,136,337 A * 10/2000 Kondo ................ A61K 9/0031
                                               424/436
2002/0115992 A1* 8/2002 Utley ................ A61B 18/1206
                                               606/41
2004/0192658 A1* 9/2004 Hunter .................... A61L 31/16
                                               514/152

OTHER PUBLICATIONS

Rayment et al., "Investigation of the distribution and function of α-adrenoceptors in the sheep isolate internal anal sphincter," British Journal of Pharmacology (2010) 160: 1727-140.*
Berge et al., "Pharmaceutical Salts," Journal of Pharmaceutical Sciences, Jan. 1977, 66(1): pp. 1-19.*
Lubowski et al., Internal anal sphincter in neurogenic fecal incontinence, Gastroenterology, vol. 95, No. 4, pp. 997-1002, 1988.

* cited by examiner

*Primary Examiner* — Sreeni Padmanabhan
*Assistant Examiner* — Jody Karol
(74) *Attorney, Agent, or Firm* — Greenberg Traurig, LLP

(57) ABSTRACT

Methods for treating fecal incontinence by administering to a subject in need thereof compositions including oxymetazoline as an active ingredient. Kits including compositions of oxymetazoline suitable for topical application, for the treatment of fecal incontinence.

7 Claims, 1 Drawing Sheet

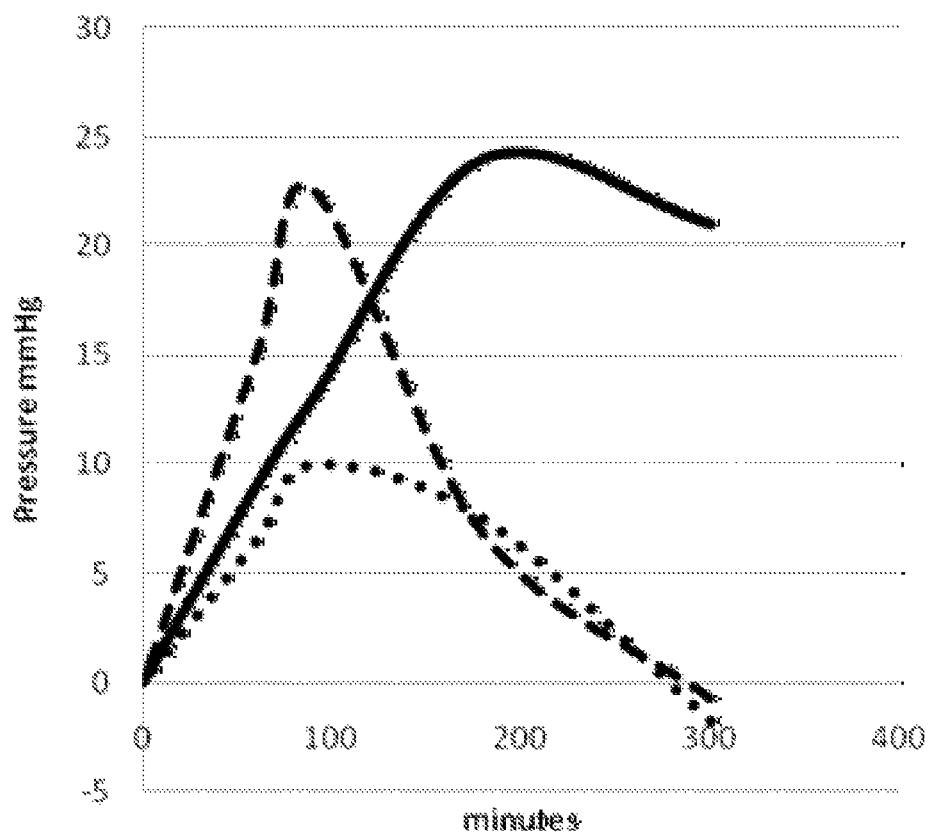

OXYMETAZOLINE FOR THE TREATMENT OF ANO-RECTAL DISORDERS

CROSS REFERENCE TO RELATED APPLICATIONS

This application is a divisional of U.S. patent application Ser. No. 14/063,759, filed on Oct. 25, 2013, which is a continuation of International Patent Application Serial No. PCT/IL2012/050148, filed on Apr. 24, 2012, which claims priority to U.S. Provisional Patent Application Ser. No. 61/478,949, filed on Apr. 26, 2011, the entire contents of which are hereby incorporated by reference in their entirety.

FIELD OF THE INVENTION

The present invention provides methods for treating ano-rectal disorders, specifically, fecal incontinence, by administering to a subject in need thereof compositions comprising oxymetazoline as an active ingredient. The present invention further provides kits comprising compositions of oxymetazoline suitable for topical application, for the treatment of ano-rectal disorders.

BACKGROUND OF THE INVENTION

Fecal incontinence is a common disorder in men and women, though more prevalent in women. The mechanisms causing anal incontinence usually involve reduced resting tone of the external and internal anal sphincters, and damage in the levator ani muscles, especially, the puborectalis muscle.

Conventional treatments of fecal incontinence include pelvic floor rehabilitation by exercises or surgical interventions and drug therapy. Biofeedback training is one of the treatments involving muscle strengthening exercises to improve anal canal resting and squeeze pressure, and to improve the symmetry of anal canal function.

Drug therapy is mostly directed to improve stool consistency and includes the use of morphine and loperamide among others. Drug therapy also includes administration of codeine phosphate to reduce gut motility (peristalsis), or laxatives to soften stools and relieve constipation. Therapy with sodium valproate was found to be useful in the treatment of minor incontinence after ileoanal anastomosis (Kusunoki et al., Surgery, 1990, 107:311-315). It was also shown that in vitro contractile response of the internal anal sphincter to noradrenaline is decreased in incontinence (e.g. Speakman et al., Digestive Diseases and Sciences, 1993, 38(11):1961-1969). Therapy with Solesta™, a viscous biocompatible bulking agent, was shown to be superior to sham treatment, resulting in 50% reduction of incontinence episodes.

Yet, the most common form of treatment is surgical repair, such as, the creation of a neo-sphincter which involves grafting on muscle from other parts of the anus, or a colostomy. However, success rates of surgeries, such as external anal sphincteroplasty, are around 50% or less.

Recent drug therapies directed to increase the anal resting pressure of a patient having a reduced anal resting pressure are disclosed in U.S. Pat. Nos. 6,635,678 and 7,781,444. Therapy according to these publications involves topical administration in and/or around the anal canal of a patient a composition comprising at least 5% w/w of an α-adrenergic agonist, particularly, noradrenalin, methoxamine and phenylephrine. However, according to these publications no significant increase in the maximum resting pressure was observed for phenylephrine concentrations below 10%, where the recommended concentrations are of 10-30% phenylephrine.

Oxymetazoline is an α-adrenergic agonist commercially known for long as a topical decongestant in the form of nasal sprays, such as, Afrin™ (e.g. U.S. Pat. No. 6,824,762). Topical application of oxymetazoline was also suggested for treating sympathetically maintained pain in peripheral tissues (e.g. RE 41,998), for reducing or eliminating pain associated with a syringe, needle stick, or lancet stick as a vasoconstrictor combined with local anesthetic (e.g. U.S. Pat. No. 7,883,488) and for ameliorating telangiectasias (U.S. Pat. No. 7,838,563) among other uses.

To date, no particularly efficient drug therapy for treating ano-rectal disorders, such as, fecal incontinence is known.

SUMMARY OF THE INVENTION

The present invention provides compositions, methods and kits for treating ano-rectal disorders, such as, fecal incontinence. More specifically, the invention is drawn to the advantageous topical use of oxymetazloine and salts or derivatives thereof, for the treatment ano-rectal disorders.

The present invention is based in part on the unexpected increase in resting anal pressure obtained upon local administration of relatively low concentrations of oxymetazloine. Surprisingly, the inventors of the present invention have found that unlike other α-adrenergic agonists, specifically, pheynilephrine, which either have a short term effect or does not exhibit a pronounced effect on a resting anal pressure, local administration of oxymetazoline provides a long term pronounced increase of the resting anal pressure. Advantageously, the improved effect of oxymetazoline was exerted by only 1 mg (0.1%) of oxymetazoline, a dose that is more than one order of magnitude lower than the less effective doses of phenylephrine (40 mg and 80 mg) tested by the inventors. Moreover, the dose of oxymetazoline which was found effective is lower by more than 2 orders of magnitude from the prior art doses of other α-adrenergic agonists (e.g. U.S. Pat. No. 6,635,678 and U.S. Pat. No. 7,781,444 which recommend using doses of 10% to 30% of phenylephrine for obtaining a significant increase in the mean resting pressure). The use of such low concentrations of oxymetazoline is particularly advantageous in view of the concentration dependent cardiovascular side effects known to be exerted by α-adrenergic agonists.

Another advantage exerted by the method of the invention is in the release of patients suffering from anal leakage from the need to undergo major surgery. Thus, oxymetazoline's effect in increasing the resting anal pressure addresses the desired need for non-invasive effective therapeutic means for the treatment of ano-rectal disorders.

Accordingly, in a first aspect the present invention provides a method for treating an ano-rectal disorder, comprising administering to a patient in need thereof a pharmaceutical composition comprising as an active ingredient oxymetazoline or a pharmaceutically acceptable salt or derivative thereof, wherein the concentration of the active ingredient is about 0.1%.

The term "about 0.1%" as used herein refers to concentrations within the range of 0.05% to 1%. That range was found effective for increasing the anal resting pressure of a patient in need thereof and at the same time safe in terms of cardiac disorders.

According to one embodiment, the active ingredient is oxymetazoline hydrochloride.

According to another embodiment, the concentration of the active ingredient is within the range of 0.05% to 1%. According to a particular embodiment, the active ingredient is oxymetazoline hydrochloride and the concentration of oxymetazoline hydrochloride is within the range of 0.05-1%, or within the range of 0.08-0.8% or about 0.1%. Each possibility is a separate embodiment of the invention.

According to yet another embodiment, treating according to the present invention is effective for at least 4 hours.

According to yet another embodiment, the composition further comprises at least one carrier, diluent, excipient or combinations thereof. Each possibility is a separate embodiment of the invention.

According to yet another embodiment, the pharmaceutical composition is selected from the group consisting of: long acting, controlled release formulation, a sustained release formulation, bioadhesive formulation, mucoadhesive formulation, and a slow release formulation. Each possibility is a separate embodiment of the invention.

According to yet another embodiment, the ano-rectal disorder is selected from the group consisting of: fecal incontinence, anorectal fistula, rectal prolapsed and ileal pouch-anal anastomosis. Each possibility is a separate embodiment of the invention.

According to yet another embodiment, the pharmaceutical composition is applied locally to any one or more of the locations selected from the group consisting of the internal anal sphincter, external anal sphincter, inside the anal canal and the anoderm. Each possibility is a separate embodiment of the invention.

According to yet another embodiment, the composition is in a dosage form selected from the group consisting of: gel, ointment, mousse, cream, paste, spray and suppository. Each possibility is a separate embodiment of the invention.

According to yet another embodiment, treating an ano-rectal disorder is selected from the group consisting of: preventing the occurrence of an ano-rectal disorder, reducing or preventing fecal incontinence, increasing the resting anal pressure, maintaining a high resting anal pressure for at least one hour, strengthening the anal sphincter muscles thereby preventing leakage and improving the rectum sensation. Each possibility is a separate embodiment of the invention.

It is to be understood that "high resting anal pressure" as used herein is not necessarily limited to a particular value or measuring means but rather refers to an anal squeeze pressure required to prevent fecal leakage.

According to yet another embodiment, the method further comprises administering one or more additional therapeutic agent in combination with oxymetazoline. According to yet another embodiment, the additional therapeutic agent is selected from the group consisting of: nitric oxide (NO) synthase inhibitor, prostaglandin F2α, dopamine, morphine, opium, loperamide, β-blockers, sodium valproate, codeine phosphate and 5-Hydroxytryptamine. Each possibility is a separate embodiment of the invention.

According to yet another aspect, the present invention provides a method for treating fetal incontinence comprising administering to a subject in need thereof a composition comprising as an active ingredient oxymetazoline.

According to yet another aspect, the present invention provides a method for treating an ano-rectal disorder comprising administering to a subject in need thereof a combined therapy comprising oxymetazoline or a pharmaceutically acceptable salt thereof and an additional therapeutic agent selected from the group consisting of: NO synthase inhibitor, prostaglandin F2α, dopamine, morphine, opium, loperamide, β-blockers, sodium valproate, codeine phosphate and 5-Hydroxytryptamine. Each possibility is a separate embodiment of the invention.

According to one embodiment, the oxymetazoline and the additional therapeutic agent are administered in fixed intervals, at variable intervals, sequentially or concurrently. Each possibility is a separate embodiment of the invention. According to yet another embodiment the oxymetazoline and the additional therapeutic agent are administered in a single dosage form.

According to yet another embodiment, the oxymetazoline is oxymetazoline hydrochloride.

According to yet another embodiment, the concentration of oxymetazoline hydrochloride is within the range of 0.05 to 1%.

According to yet another embodiment, the combined therapy is effective for at least 4 hours.

According to yet another aspect, the present invention provides a kit for treating an ano-rectal disorder in a subject in need thereof comprising
(a) a first dosage form comprising oxymetazoline or a pharmaceutically acceptable salt or derivative thereof, wherein the concentration of oxymetazoline in the first dosage form is within the range of 0.05 to 1%; and
(b) means for storing the dosage form.

According to one embodiment, the means for storing the dosage form, include, but are not limited to, a container suitable for long storage and blister packaging for pharmaceuticals, among others.

According to another embodiment, the kit further comprises a second dosage form comprising a therapeutic agent selected from the group consisting of: NO synthase inhibitor, prostaglandin F2α, dopamine, morphine, opium, loperamide, β-blockers, sodium valproate, codeine phosphate and 5-Hydroxytryptamine. Each possibility is a separate embodiment of the invention. According to another embodiment, the first and second dosage forms are contained in a single container. According to yet another embodiment, the first dosage form and the second dosage form are contained in separate containers. According to yet another embodiment, the first dosage form comprises oxymetazoline hydrochloride.

According to yet another aspect, the present invention provides a pharmaceutical composition comprising as an active ingredient an oxymetazoline or a pharmaceutically acceptable salt or derivative thereof for use in the treatment of an ano-rectal disorder, wherein the concentration of the active ingredient is within the range of 0.05% to 1%.

According to some embodiments, the pharmaceutical composition further comprises one or more additional therapeutic agent in combination with oxymetazoline. According to yet another embodiment, the additional therapeutic agent is selected from the group consisting of: nitric oxide (NO) synthase inhibitor, prostaglandin F2α, dopamine, morphine, loperamide, β-blockers, sodium valproate, codeine phosphate and 5-Hydroxytryptamine.

According to yet another aspect, the present invention provides a pharmaceutical composition for use in the treatment of an ano-rectal disorder in combination with an additional therapeutic agent selected from the group consisting of: NO synthase inhibitor, prostaglandin F2α, dopamine, morphine, loperamide, β-blockers, sodium valproate, codeine phosphate and 5-Hydroxytryptamine.

According to yet another aspect, the present invention provides a combined therapy comprising the pharmaceutical composition of the present invention, and an additional therapeutic agent selected from the group consisting of: NO synthase inhibitor, prostaglandin F2α, dopamine, morphine, loperamide, β-blockers, sodium valproate, codeine phosphate and 5-Hydroxytryptamine for use in the treatment of an ano-rectal disorder.

According to one embodiment, the active ingredient is oxymetazoline hydrochloride.

According to yet another embodiment, the ano-rectal disorder is selected from the group consisting of: fecal incontinence, anorectal fistula, rectal prolapsed and ileal pouch-anal anastomosis. According to yet another embodiment, the ano-rectal disorder is fecal incontinence.

According to yet another embodiment, the composition is in a dosage form selected from the group consisting of: gel, cream, paste, spray suppository, mousse, emollient, powder, solution, suspension and foam.

According to yet another embodiment, the concentration of the oxymethazoline is within the range of 0.05% to 1%. According to yet another embodiment, the concentration of oxymethazoline is within the range of 0.08 to 0.8%.

According to yet another embodiment, the pharmaceutical composition is effective for at least 4 hours.

According to yet another embodiment, the oxymetazoline and the additional therapeutic agent are administered in fixed intervals, at variable intervals, sequentially or concurrently. According to another embodiment, the oxymetazoline and the additional therapeutic agent are in a single dosage form.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 represents the mean relative resting anal pressure exerted by topical application of 1 mg oxymetazoline (solid line), 40 mg phenylephrine (dotted line) and 80 mg phenylephrine (broken line).

DETAILED DESCRIPTION OF THE INVENTION

Fecal incontinence is a disorder common to both genders although more common in women after childbirth, presumably as a result of trauma to pelvic floor muscles, supporting fascia and nerves. Fecal incontinence affects an estimated 7.6 percent of women between the ages of 30 to 90. This prevalence increases with age, affecting 3.6 percent of women between the ages of 30 to 39 and 15.2 percent of women between the ages of 80 to 90.

Fecal incontinence may occur as the result of several mechanisms, including direct damage to the internal or external anal sphincters (from iatrogenic episiotomy or spontaneous lacerations during vaginal delivery), or to the levator ani muscles. It may also result from indirect injury of these muscles through denervation of the nerves that supply these muscles. Treatment of this problem has centered on pelvic floor rehabilitation, dietary changes, or surgical correction. As detailed below, surgery has been used to treat specific defects in the anal sphincters, such as, external anal sphincteroplasty. Success rates of only 50% or less are generally reported for these procedures on long-term follow-up.

It has been shown that two thirds of patients with idiopathic fecal incontinence had a decreased anal resting pressure resulting from an abnormal internal sphincter function. In many incontinent patients, the internal anal sphincter was found to be abnormally thin, while others had an external anal sphincter defect.

The conservative interventions for treating fecal incontinence consist mainly of changes in lifestyle (sport, work, giving up smoking, modification to the diet and fluid intake); measures of assistance with daily activities (adaptation of clothing, absorbent products, bags, stoppers, adaptation of the fitting out of toilets, control of odor, skincare); intestinal control and a retraining programs (planning for going to the toilet, resisting urgent need, behavior modification, rectal irrigation, digital stimulation or the like, abdominal massage); and functional readaptation by stimulation (and/or pelvic or sphincter exercises). This conditioning method, which uses visual, verbal or auditory signals, improves rectal sensation and rectoanal coordination, and brings about contraction of the external anal sphincter. The success rates of various series range from 40% to 85%, which rates could probably be predicted by the patient's motivation and the cause of the pathology rather than by the duration of fecal incontinence, manometric or endoanal ultrasound measurements or else the functional readaptation technique used.

Although the conservative measures are simple to implement, they are often of limited effectiveness.

Several techniques making use of medical devices exist which can benefit patients suffering from fecal incontinence. For example, the "proton continence" device (Incontinence Control Devices, Inc., Kingwood, Tex.) is a flexible catheter with a photosensor and a balloon, which can be inserted into the rectum in order to send a signal warning of the arrival of stools. This device has shown an improvement in continence in certain patients. Moreover, submucosal injections of a wide variety of agents have been used to increase internal anal sphincter tone (silicone, silicone-based agents, this include, carbon-coated beads, carbon-coated zirconium oxide beads (Durasphere™), autologous fat and collagen crosslinked with glutaraldehyde, polytetrafluoroethylene. These devices have shown a partial symptomatic improvement in resting anal pressure and in continence.

The Secca™ procedure (Curon Medical, Inc., Sunnyvale, Calif.) uses radiofrequency energy controlled by the temperature of the anal canal and of the distal rectum in order to create scarring of the external anal sphincter and tissue fibrosis. In a multicentre prospective study by Efron et al. an improvement in fecal incontinence and in the quality of life with disappearance of symptoms in 60% of patients. Takahashi et al. have reported similar results after a follow-up of patients for 2 years.

Another treatment for faecal incontinence is sacral nerve stimulation (SNS) which, by "neuromodulating" the somatic voluntary nerves and the afferent and efferent autonomic nerves, makes it possible to stimulate both the somatic and the autonomic innervation of the pelvic organs and of the anorectal region, through the sacral and pudendal nerves. The results published with this procedure are encouraging, with a marked improvement in continence of up to 100% and restoration of complete continence in 41% to 75% of cases.

All these procedures have certain effectiveness, but their use is restrictive.

Drug treatments for fecal incontinence are limited to anti-diarrhea agents and to laxatives, enemas and suppositories, which make it possible to evacuate the bowel. At low dose, amitryptiline (tricyclic anti-depressant), via its anti-cholinergic and serotoninergic activities, could also improve continence. On the other hand, no medicament that acts on sphincter tone is currently registered specifically for the treatment of fecal incontinence.

The viscous bulking agent, Solesta™, has been suggested for treating fecal incontinence in adult patients who have failed conservative therapy. Solesta™ is injected in the deep submucosal layer in the proximal part of the high pressure zone of the anal canal, about 5 mm above the dentate line. A total of four submucosal injections of 1 mL Solesta™ are administered at each treatment session. However, Solesta™ was shown to be superior over placebo in 50% of the treated subjects.

At the current time, the only alternative in patients suffering from external sphincter disorders but without a neurological condition (intact pudendal nerves) is, after failure of conservative therapies, surgery. An artificial anal sphincter has been used to bypass these muscles, though this surgery involves fairly extensive dissection and requires the patient to depress a subcutaneous valve which temporarily deflates the sphincter cuff and allows voluntary defecation. This procedure is performed in very few centers in the U.S., and even in experienced hands, complications occur frequently.

Dynamic graciloplasty, which involves mobilization and wrapping of the gracilis muscle around the anorectum is another accepted procedure although is remains complex and requires extensive experience to obtain good results. More recently, sacral nerve stimulation has been used with some success to treat fecal incontinence, though the mechanism of success in these patients remains unclear, and may not be appropriate in women with obvious anatomic abnormalities, such as anal sphincter or levator muscle disruptions.

Further discussion of the innervations and control of the internal anal sphincter and drugs which can increase or decrease the normal anal resting pressure, is discussed in various text books (e.g., Coloproctology and the Pelvic Floor, Butterworths, second edition, 1992, Chapter 3, p. 37-53; Automic Control of Internal Anal Sphincter). Implantations of devices intended to improve fecal incontinence, for example, microstimulators for implantation thereof in the anal sphincter for treating fecal incontinence, are disclosed for example, in U.S. Pat. No. 7,871,415.

Other than anal incontinence, many women report on symptoms of bowel dysfunction, such as constipation and incomplete bowel emptying. For some women, these symptoms are due to either an anterior rectocele (a hernia of the rectum into the vaginal canal), or due to a defect in the levator ani muscles, which results in descent of the levator plate and/or perineum with abdominal straining. In addition, patients may be noted to have a defect in the posterior aspect of the rectum, or a posterior rectocele. There are very few treatment options for this condition, though retrorectal levatorplasty has been used in the past. In this procedure, an incision is made between the anus and the coccyx and the levator muscles are exposed bilaterally. Sutures are then placed in the levator muscles to plicate them together in the midline. Pelvic organ prolapse is a condition where organs, such as the uterus, the rectum, or the bladder, fall down or slip out of place within a person's body. It is commonly used in reference to organs protruding through a woman's vagina, but prolapse may occur within men as well.

The method of the invention appear to treat ano-rectal disorders, such as, fecal incontinence by increasing the resting pressure of the internal anal sphincter using topical administration of the α-agonist oxymetazoline or salts thereof.

Alpha-agonists are known to cause side effects, of particular alert are cardiovascular disorders. Because alpha1-agonists produce systemic vasoconstriction, the effort on the heart increases. If the coronary circulation is impaired, as in patients with coronary artery disease, the decrease in myocardial oxygen supply/demand ratio can precipitate angina. In view of the above, the inventors of the present invention searched for an α-agonist that does not exert a cardiac side effect, while being effective in increasing the resting anal pressure. Surprisingly, oxymetazoline was found the best candidate as it was effective in low doses of about 0.1% but did not induce any changes in the diastolic blood pressure, systolic blood pressure or in the heart rate (see Example 2).

Oxymetazoline, also known as 3-(4,5-dihydro-1H-imidazol-2-ylmethyl)-2,4-dimethyl-6-tert-butyl-phenol, is an α-adrenergic agonist commercially available over the counter in its hydrochloride salt form, as a topical decongestant in the form of nasal sprays. Oxymetazoline seems to exert its therapeutic action by nonselectively agonizes adrenergic receptor, which are widely expressed in vascular beds, thereby causing vasoconstriction. Vasoconstriction of vessels results in relief of nasal congestion by increasing the diameter of the airway lumen; and by reducing fluid exudation from postcapillary venules.

Methods for measuring resting anal pressure include manometry (to determine the maximum resting anal pressure). In this method a water-filled microballoon system connected to a plastic rigid catheter and transducer and then to a pen chart recorder or pressure sensitive electrodes, which are connected to an amplifier/monitor, is used. Maximum resting anal pressure is obtained using a station pull through technique where a catheter is taped to the buttock and a continuous reading being performed until a steady anal pressure is achieved. After a drug is administered, continuous pressure readings may be taken, for example, between 15 and 31 minutes. Pulse rate and blood pressure may be monitored and the subject may be questioned for adverse effects, such as, headache, anxiety, palpitations and abdominal or anal pain.

A preferred oxymetazoline according to the present invention is an oxymetazoline salt, such as, oxymetazoline hydrochloride salt. Oxymetazoline hydrochloride has the chemical name 6-tert-butyl-3-(2-imidazolin-2-ylmethyl)-2,4-dimentylphenol hydrochloride (CAS Registry No. 2315-02-8). According to U.S. Patent Application, Publication No. 2009/0281156, by lowering the pH of formulations containing oxymetazoline HCl, photodegradation level of oxymetazoline HCl is significantly reduced, even in the presence of destabilizing excipients, such as PVPs or PEGs.

The composition further comprises a least one carrier, diluent, excipient or combinations thereof.

Oxymetazoline is soluble in aqueous and non aqueous media and accordingly, oxymetazoline solution may contain an aqueous carrier comprising: 70 to 90% by weight/volume of water; 0.10 to 5.00% by weight/volume of an aromatic alcohol; 0.01 to 0.3% by weight/volume of a non-mercurial antimicrobial preservative; 0 to 10% by weight/volume of a moisturizing agent; a sufficient amount of a pharmaceutically acceptable buffer to maintain the pH of the composition within the range of about 4.00 to 6.00; and/or other agents as deemed necessary to enhance flavor or to enhance the functional capabilities of the primary agent.

In one embodiment, the pharmaceutical composition is formulated as long acting, controlled release formulation. In another embodiment, the pharmaceutical composition is formulated as a sustained release formulation. In another embodiment, the pharmaceutical composition is a bioadhesive formulation or a mucoadhesive formulation.

Controlled or sustained release formulations allowing for extended or slow release of the active components over a predetermined time period may be formulated using procedures known in the art. Alternatively, the compositions may be formulated as immediate release formulations.

Techniques for formulation and administration of drugs may be found in "Remington's Pharmaceutical Sciences," Mack Publishing Co., Easton, Pa., latest edition, which is incorporated herein by reference.

The inert ingredients (e.g. excipient or a carrier) and manner of formulation of the pharmaceutical compositions are conventional. The active compound is formulated into pharmaceutical compositions and administered in a variety of forms appropriate for the method of the invention including, but not limited to liquid, semisolid, powders, suppositories, sprayable solutions, gel, ointment, mousse, cream or paste.

Suitable excipients include, but are not limited to lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methylcellulose.

The formulations may additionally include lubricating agents, such as, talc, magnesium stearate and mineral oil; wetting agents; emulsifying and suspending agents; preserving agents such as methyl- and propyl hydroxybenzoates.

Additional excipients that are particularly suitable for the manufacture of suppositories, include, but are not limited to, coconut oil, cocoa butter, polyethylene glycol, propylene glycol, glycerinated gelatin, hydrogenated vegetable oil, fatty acid esters of a polyethylene glycols, glycolsurfactant polyethylene glycol, a polyoxyethylene derivatives of sorbitan monostearate or polyoxyl-40 stearate, and combinations thereof. Each possibility is a separate embodiment of the invention.

The liquid forms in which the compositions of the present invention may be incorporated, for administration to internal anal sphincter, external anal sphincter, inside the anal canal and the anoderm, include aqueous solutions, aqueous or oil suspensions, and similar pharmaceutical vehicles. The procedure for introducing the compositions of the invention into the rectum and colon may involve use of enema devices.

Suitable pharmaceutical compositions for topical application according to the invention include, may be in the form of ointment, gel, mousse, drops, emollient, powder, solution, suspension, foam, suppository, cream, lotion, paste, spray, aerosol or oil. Examples of suitable vehicles include, but are not limited to aquaphor, neobase, propylene glycol, glycerin and the like. Combinations of two or more of these vehicles can also be used. Each possibility is a separate embodiment of the invention.

Other suitable forms for topical application of the pharmaceutical compositions of the invention include bioadhesive such as mucoadhesive formulations. Adhesion of formulation to the mucosal tissue creates an intimate and prolonged contact at the administration site, resulting in enhanced absorption and controlled release. Mucoadhesive formulations usually include mucoadhesive polymers, such as, cross-linked poly(acrylic acid), glyceryl monooleate, polyvinyl chloride and glyceryl monolinoleate. More information on mucoadhesive formulations may be found in Edsman et al. (JPP, 2005, 57: 3-22) among others.

Preferred excipients include propylene glycol, polyethylene glycol and the like, as these compounds prevent bacterial growth in the composition.

In one embodiment, the inventive composition is provided as a cream, sometimes referred to as an emulsion. Suitable creams may comprise, in addition to the active ingredient, a stiffening agent, a release modifier and a polar solvent (water or a substitute thereof).

The stiffening agent used for creams may comprise a fatty alcohol, having a hydrocarbon chain containing 16 to 18 carbon atoms and having a melting point in pure state of about 45 to 65° C. Alternatively, the stiffening agent may be cetyl alcohol, stearyl alcohol, or cetostearyl alcohol, preferably stearyl alcohol. Each possibility is a separate embodiment of the invention.

In such creams, the release modifier may comprise a fatty alcohol, a fatty alcohol glycol ether, or a fatty acid sorbitane ester, having a hydrocarbon chain containing 12 to 18 carbon atoms and having a melting point in pure state of about −10 to 40° C.

Alternatively, the release modifier may be dodecanol, tetradecanol, palmitoyl alcohol, oleyl alcohol, linoleyl alcohol, polyoxyethylene lauryl ether, polyoxyethylene myristyl ether, polyoxyethylene cetyl ether, polyoxyethylene stearyl ether, sorbitane monolaurate, sorbitane monooleate, or glyceryl monooleate, preferably oleyl alcohol. Each possibility is a separate embodiment of the invention.

In a preferred cream, the release modifier may comprise a fatty alcohol, having a hydrocarbon chain containing 12 to 18 carbon atoms and having a melting point in pure state of about −10 to 40° C. Alternatively, the release modifier may be dodecanol, tetradecanol, palmitoyl alcohol, oleyl alcohol, or linoleyl alcohol, preferably oleyl alcohol.

The release modifier may be present in the cream in an amount of about 1 to 12% by weight, preferably about 2 to 10% by weight, based on the weight of the composition.

In the cream, water or a substitute thereof is present. Suitable substitutes are glycerol or ethanol. Each possibility is a separate embodiment of the invention.

In another embodiment, the inventive composition is present as an ointment. Such ointment may comprise, in addition to the active ingredient, the stiffening agent and the release modifier, and a polar solvent as described above. Each possibility is a separate embodiment of the invention.

In an ointment, the stiffening agent may comprise a fatty alcohol, having a hydrocarbon chain containing 16 to 18 carbon atoms and having a melting point in pure state of about 45 to 65° C. Alternatively, the stiffening agent may be cetyl alcohol, stearyl alcohol, or cetostearyl alcohol, preferably stearyl alcohol. Cetomacrogol emulsifying wax is a source of cetostearyl alcohol and thus a convenient way of providing a stiffening agent in the ointment.

The release modifier may comprise a fatty alcohol, a fatty alcohol glycol ether, a fatty acid alkyl ester, a fatty acid glycerol ester, or a fatty acid sorbitane ester, having a hydrocarbon chain containing 12 to 18, carbon atoms and having a melting point in pure state of about −10 to 40° C. Alternatively, the release modifier may be dodecanol, tetradecanol, palmitoyl alcohol, oleyl alcohol, linoleyl alcohol, polyoxyethylene lauryl ether, polyoxyethylene myristyl ether, polyoxyethylene cetyl ether, polyoxyethylene stearyl ether, sorbitane monolaurate, sorbitane monooleate, or glyceryl monooleate, preferably oleyl alcohol. Each possibility is a separate embodiment of the invention.

The release modifier may also comprise a fatty alcohol, a fatty alcohol glycol ether, or a fatty acid sorbitane ester, having a hydrocarbon chain containing 12 to 18 carbon atoms and having a melting point in pure state of about −10 to 40° C.

In some embodiments, the release modifier of the ointment may be dodecanol, tetradecanol, palmitoyl alcohol, oleyl alcohol, or linoleyl alcohol. Each possibility is a separate embodiment of the invention.

The release modifier may be present in the ointment in an amount of about 5% to 15% by weight, or about 8% to 12% by weight, based on the weight of the composition.

When a topical preparation is an ointment, cream, gel or paste in a tube, the instructions for use may recommend an appropriate amount to be used, for example, to squeeze about 2-3 cm of preparation from the tube. A topical preparation may be provided in a container that comprises a pump and metered dosing device to assist correct dosing. In general, from about 0.5 to about 3 ml, for example, about 1 ml, is a suitable volume of a cream, gel or ointment for topical application. However, when applying a topical preparation, especially when using the finger, it is often difficult to administer a precise dose. Use of an applicator may give more precise dosing.

The instructions for use of the pharmaceutical composition of the present invention should indicate the recommended site of application, for example, whether the preparation should be applied to the skin around the anus or whether the preparation should also be inserted into the anus. Preferably, the instructions for use of the pharmaceutical composition of the present invention should further indicate the recommended dose and treatment regimen.

In one embodiment, the composition of the invention may comprise aside from oxymetazoline, an agent selected from the group consisting of: benzalkonium chloride, benzylalcohol, edentate disodium, carboxymethylcellulose sodium, microcrystalline cellulose, polyethylene glycol, povidone, sodium phosphate dibasic, sodium phosphate monobasic and water. Each possibility is a separate embodiment of the invention.

The composition of the invention is intended for the treatment of any ano-rectal disorder, including, but not limited to, fecal incontinence, anorectal fistula, rectal prolapsed and ileal pouch-anal anastomosis. Each possibility is a separate embodiment of the invention.

The ileal pouch-anal anastomosis, also known as an ileo-anal pouch, restorative proctocolectomy, ileal-anal pullthrough, j-pouch, s-pouch, w-pouch or an internal pouch, is an internal reservoir constructed for patients who have had their large intestine surgically removed due to disease or injury.

The ileal pouch-anal anastomosis is usually situated where the rectum would normally be and is formed by folding loops of small intestine (the ileum) back on themselves and stitching or stapling them together. The internal walls are then removed thus forming a reservoir. The reservoir is then stitched or stapled into the perineum where the rectum was.

Diseases and conditions of the large intestine which may require surgical removal of the large intestine include: ulcerative colitis, crohn's disease, familial adenomatous polyposis, colon cancer and toxic megacolon.

The term "treating an ano-rectal disorder" as used herein refers to any one of the following: preventing the occurrence of an ano-rectal disorder, reducing or preventing fecal incontinence, increasing the resting anal pressure, maintaining a high resting anal pressure for at least one hour, strengthening the anal sphincter muscles thereby preventing leakage, improving the rectum sensation, increasing the tone of the pyloric sphincter, increasing the tone of smooth muscle of the gastrointestinal tract and increasing the tone of a sphincter of the gastrointestinal tract. Each possibility is a separate embodiment of the invention.

It is to be understood that "high resting anal pressure" as used herein is not necessarily limited to a particular value or measuring means but rather refers to an anal squeeze pressure required to prevent fecal leakage.

The method of the invention may further comprise combined therapy, namely, a combination of two therapeutic compounds for treating a patient afflicted with an ano-rectal disorder. Thus, the method of the invention may further include administering at least one additional therapeutic agent in combination with oxymetazoline. The additional therapeutic agent may include any one or more of the following agents: nitric oxide (NO) synthase inhibitor, prostaglandin $F_{2\alpha}$, dopamine, morphine, loperamide, β-blockers, sodium valproate, codeine phosphate and 5-Hydroxytryptamine. Each possibility is a separate embodiment of the invention.

Examples of suitable prostaglandin $F_{2\alpha}$ include dinoprost and carboprost. Examples of suitable NO synthase inhibitors include $N^G$-monomethyl-L-arginine (L-NMMA), and $N^G$-nitro-L-arginine methyl ester (L-NAME).

The prostaglandins, along with thromboxanes and leukotrienes are all derived from 20-carbon polyunsaturated fatty acids and are collectively termed eicosanoids. $F_{2\alpha}$ prostaglandins are derived in vivo from the endoperoxide prostaglandin $H_2$ which is in turn derived from leukotrienes. Clinically, $F_{2\alpha}$ prostaglandins, such as, dinoprost and carboprost, are used as uterine stimulants in the termination of pregnancy, missed abortion or the induction of labor.

The present invention further encompasses methods for treating an ano-rectal disorder by administering to a subject in need thereof a combined therapy comprising oxymetazoline or a pharmaceutically acceptable derivative or salt thereof and an additional therapeutic agent selected from the group consisting of: NO synthase inhibitor, prostaglandin $F_{2\alpha}$, dopamine, morphine, loperamide, β-blockers, sodium valproate, codeine phosphate and 5-Hydroxytryptamine.

In some embodiment, the oxymetazoline and the additional therapeutic agent are administered in fixed intervals, at variable intervals, sequentially or concurrently. Each possibility is a separate embodiment of the invention. Furthermore, the oxymetazoline and the additional therapeutic agent may be administered in a single dosage form.

Whether administered alone or in combination with another active ingredient, the therapeutic effect of oxymetazoline on the ano-rectal disordered is maintained for at least 4 hours, or even for at least 5 hours.

According to further aspects the present invention provides kits suitable for use in methods of treating ano-rectal disorders, in a subject. Thus, in another embodiment, there is provided a kit comprising (a) a first dosage form comprising oxymetazoline or a pharmaceutically acceptable derivative or salt thereof; and (b) container means to contain the dosage form.

The kit may further comprise a second dosage form comprising a therapeutic agent selected from the group consisting of: NO synthase inhibitor, prostaglandin F2α, dopamine, morphine, loperamide, β-blockers, sodium valproate, codeine phosphate and 5-Hydroxytryptamine.

According to some embodiments the first and second dosage forms are contained in a single container. According to other embodiments the first dosage form and the second dosage form are contained in separate containers.

The effective concentration of oxymetazoline for treating ano-rectal disorder is usually within the range of 0.05 to 1%, or within the range of 0.08 to 0.8%, or about 0.5% or about 0.1%.

Examples of dosage forms for the pharmaceutical composition of the present invention are described above. For rectal administration, dosage forms include, for example, tablets, capsules and suppositories. A metered dosing device may be provided, for example, a pump device, for dosing a predetermined volume of a topical composition, for example, a cream, ointment or gel.

The following examples are presented in order to more fully illustrate some embodiments of the invention. They should, in no way be construed, however, as limiting the broad scope of the invention.

EXAMPLES

Example 1: The Effect of Alpha Agonist on Resting Anal Pressure

Preparations of phenylephrine hydrochloride and oxymetazoline were prepared. The oxymetazoline was first dissolved in propylene glycol and then added to polyethylene glycol 1500 to obtain a solution in the concentration of 1 mg/1 mL.

The preparations were administered intraanally. The doses are expressed as both a volume of a concentration of the drug solution and also as milligrams of the active ingredient.

Resting anal pressure was determined by anorectal manometry for measuring contractility in the anus and rectum using the ManoScan 360™ catheter (Sierra Scientific Instruments).

Healthy volunteers, men and women of 18 to 55 years old received intraanal dose of 40 mg (40 mL) or 80 mg (80 mL) phenylephrine or a dose of 1 mg oxymetazoline (1 mL; 0.1%). None of the volunteers had symptoms of anal incontinence nor previous anal surgery and presumed to have intact internal and external anal sphincters. Pre-treatment mean resting pressure was 85 mmHg for the phenyephrine 40 mg group, and 81 mmHg for the phenylephrine 80 mg group.

After the application of the aforementioned doses of phenylephrine and oxymetazoline, resting anal pressure was determined at the following time intervals: for the phenyleohrine trial—prior to administration of phenylephrine and 60, 120 and 240 minutes afterwards, and for the oxyetazoline trial—before administration and 60, 180 and 300 minutes after application. The results are summarized in Tables 1 and 2 below and in FIG. 1.

TABLE 1

Resting anal pressure upon administration of phenylephrine.

| Time (minutes) | Resting anal pressure (mmHg) | | Change Relative to T = 0 | |
| --- | --- | --- | --- | --- |
| | Phenylephrine (40 mg) | Phenyl-ephrine (80 mg) | Phenylephrine (40 mg) | Phenyl-ephrine (80 mg) |
| 0 | 85 | 81 | 0 | 0 |
| 90 | 95 | 103.5 | 10 | 22.5 |

TABLE 1-continued

Resting anal pressure upon administration of phenylephrine.

| Time (minutes) | Resting anal pressure (mmHg) | | Change Relative to T = 0 | |
| --- | --- | --- | --- | --- |
| | Phenylephrine (40 mg) | Phenyl-ephrine (80 mg) | Phenylephrine (40 mg) | Phenyl-ephrine (80 mg) |
| 180 | 92.5 | 87.75 | 7.5 | 6.75 |
| 240 | 83.25 | 80.25 | 0 (±1.75) | 0 (±1.75) |

TABLE 2

Resting anal pressure upon administration of oxymetazoline.

| Time (min.) | Resting anal pressure (mmHg) | Change Relative to T = 0 |
| --- | --- | --- |
| 0 | 75 | 0 |
| 60 | 93 | 18 |
| 180 | 103 | 28 |
| 300 | 102 | 27 |

A pronounced increase in the maximum resting pressure, about 30 mmHg relative to the pressure before treatment, was observed for treatment with oxymetazoline (FIG. 1). A smaller increase in anal pressure was obtained with 80 mg phenylephrine (maximum increase of 22.5 mmHg) and much lower increase in pressure, with a maximum increase of 10 mmHg, was observed in the treatment with 40 mg phenylephrine.

The increased pressure obtained upon treatment with oxymetazoline was maintained for the duration of the recording, i.e. for at least 5 hours. However, the increased pressure obtained with 80 mg phenylephrine dropped within 3 hours nearly to the pressure obtained prior to treatment. Additionally, in less than 5 hours, the resting anal pressure dropped down to the pressure observed prior to treatment.

Treatment with 40 mg phenylephrine reached a very low increase relative to the pressure before the treatment (an increase of 10 mmHg) which gradually dropped and reached the initial (pre-treatment) resting anal pressure within less than 5 hours.

The results highlight the superiority of oxymetazoline on phenylephrine. Oxymetazoline, at a low dose of 1 mg, induced a better effect (a marked increase in resting anal pressure) which was maintained for a long time (for at least 5 hours), as compared to the effect exerted by phenylephrine at doses as high as 40 mg and 80 mg.

Example 2: The Cardiac Effect of Oxymetazoline

The effect of oxymetazoline on cardiac parameters was examined in four healthy human subjects. The results are presented in the Table 3.

TABLE 3

Resting anal pressure and cardiac parameters

| Physiological parameter | Oxymetazoline dose | | |
| --- | --- | --- | --- |
| | 0.01% | 0.1% | 0.5% |
| Change in resting anal pressure (mmHg) | 11 | 18.5 | 24.75 |

TABLE 3-continued

Resting anal pressure and cardiac parameters

| Physiological parameter | Oxymetazoline dose | | |
|---|---|---|---|
| | 0.01% | 0.1% | 0.5% |
| Change in diastolic blood pressure (mmHg) | 2 | 0 | 1 |
| Change in heart rate (beats/min) | −3 | 0 | 1 |
| Change in systolic Blood pressure (mmHg) | 6 | 5 | 3 |

The change in resting anal pressure with respect to baseline, in response to doses of 0.1% and 0.5%, was statistically significant.

The results indicate that at the low doses of oxymetazoline are highly effecting in inducing a significant increase in the resting anal pressure, these doses do not induce any cardiovascular side effect.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A method,
wherein the method treats fecal incontinence in a subject in need thereof,
wherein the method comprises: administering a therapeutically effective amount of a composition consisting essentially of oxymetazoline or a pharmaceutically acceptable salt thereof to the subject's anal cavity, to treat the fecal incontinence, wherein the composition consists essentially of 0.1% to 1% of oxymetazoline or the pharmaceutically acceptable salt thereof.

2. The method of claim 1, wherein the pharmaceutically acceptable salt is oxymetazoline hydrochloride.

3. The method of claim 1, wherein the composition includes at least one carrier, diluent, excipient, or combinations thereof.

4. The method of claim 1, wherein the composition is one of a long acting composition, a controlled release composition, a slow release composition, a sustained release composition, a bioadhesive composition, and a mucoadhesive composition.

5. The method of claim 1, wherein the composition is in a dosage form selected from the group consisting of: gel, cream, paste, spray suppository, mousse, emollient, powder, solution, suspension and foam.

6. The method of claim 1, wherein the therapeutically effective amount of the composition consists essentially of 0.1% to 0.8% of oxymetazoline or the pharmaceutically acceptable salt thereof.

7. The method of claim 1, wherein the therapeutically effective amount of the composition is sufficient to treat fecal incontinence in the subject for at least 4 hours.

* * * * *